United States Patent [19]

Basta

[11] 4,414,999

[45] Nov. 15, 1983

[54] CONTINUOUS FLUSHING DEVICE

[76] Inventor: Michael I. Basta, 503 N. Rossevelt Blvd. - Apt. A314, Falls Church, Va. 22044

[21] Appl. No.: 215,870

[22] Filed: Dec. 12, 1980

[51] Int. Cl.³ ............................................. F16K 51/00
[52] U.S. Cl. .................................. 137/240; 137/599.2; 137/605; 137/614.17; 137/614.19; 251/117; 251/122; 251/243; 604/249
[58] Field of Search ............... 137/240, 614.17, 614.18, 137/614.19, 605, 599.2; 251/122, 238, 243; 128/214 R; 138/45; 604/32, 33, 35, 248, 249, 83, 118, 149, 150

[56] References Cited

U.S. PATENT DOCUMENTS

| | | | |
|---|---|---|---|
| 990,179 | 4/1911 | Wilson et al. | 251/243 |
| 2,986,158 | 5/1961 | Gratzmuller | 137/614.19 |
| 3,605,740 | 9/1971 | Price et al. | 128/214 F |
| 3,675,891 | 7/1972 | Reynolds et al. | 251/117 |
| 3,802,662 | 4/1974 | Viguier | 604/249 |
| 3,841,354 | 10/1974 | McDonnell | 138/43 |
| 3,868,973 | 3/1975 | Bierman et al. | 138/43 |
| 3,877,428 | 4/1975 | Seagle et al. | 128/214 R |
| 3,880,401 | 4/1975 | Wiltse | 251/205 |
| 4,030,695 | 6/1977 | Curtis | 137/614.19 |
| 4,063,555 | 12/1977 | Ulinder | 604/83 |
| 4,064,908 | 12/1977 | Loe | 137/614.17 |
| 4,118,007 | 10/1978 | Scopes | 251/223 |
| 4,192,303 | 3/1980 | Young et al. | 128/214 R |
| 4,200,119 | 4/1980 | Cunningham | 251/117 |
| 4,210,178 | 7/1980 | Morse et al. | 137/625.5 |

OTHER PUBLICATIONS

Schwartz et al, "Critical Care Medicine", vol. 5, No. 2, pp. 115 and 116, Mar.–Apr. 1977.
Johnson et al, "Journal of Thoracic and Cardiovascular Surgery", pp. 675–678, 1968.
"Direct Monitoring of Blood Pressure" by Bell & Howell, 1976.

Primary Examiner—A. Michael Chambers
Attorney, Agent, or Firm—Cushman, Darby & Cushman

[57] ABSTRACT

A flow regulating assembly and components are provided for a catheter system. The assembly provides a regulated flow of medical fluid with an intermittent operator-controlled large-volume flushing flow. The assembly includes a flow-occluding piston reciprocal within a housing to move from the regulated flow position to a position completely out of the path of fluid flow from the inlet to the outlet. Actuation of the piston is from the exterior of the housing, and adjustment of the regulated flow volume is also effected from the housing exterior. The assembly components may be sterilized and fitted together in a clean room without welding or gluing being necessary.

18 Claims, 6 Drawing Figures

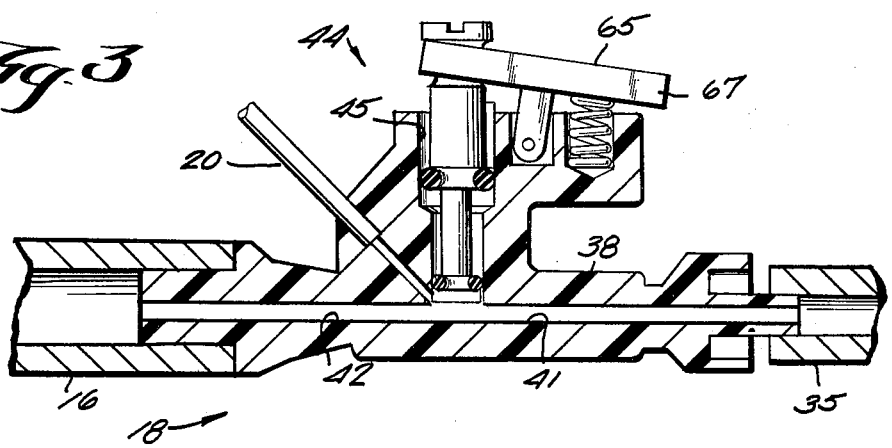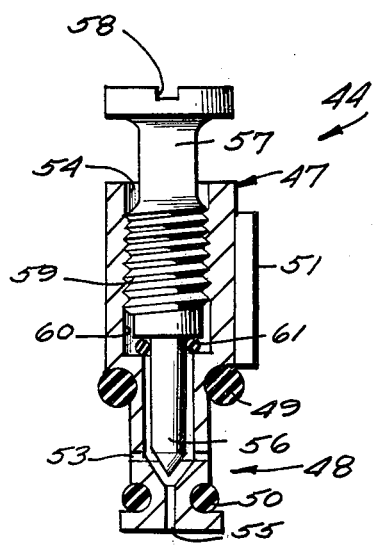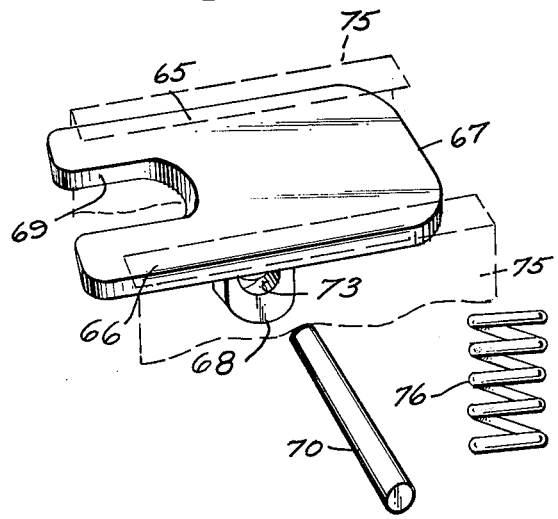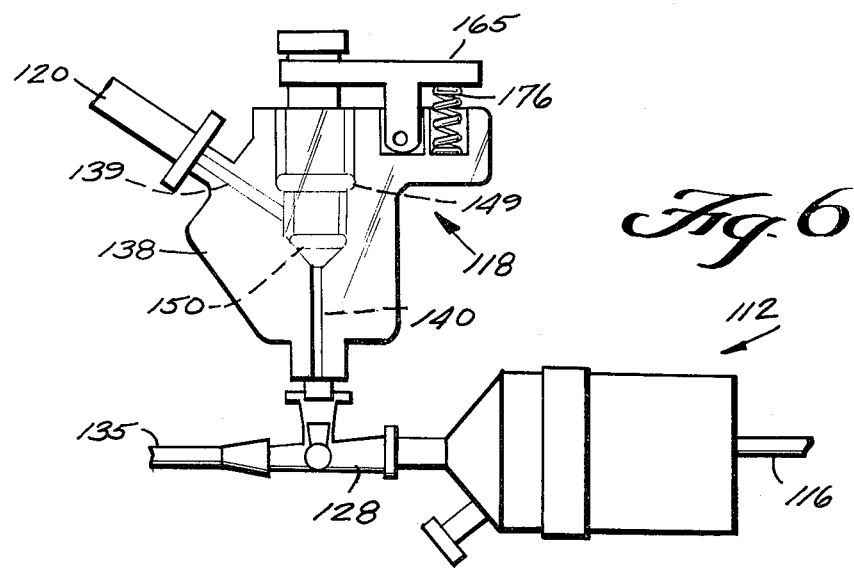

CONTINUOUS FLUSHING DEVICE

BACKGROUND AND SUMMARY OF THE INVENTION

In modern critical care/intensive care environments, it is necessary to monitor various hemodynamic functions over extended periods of time. For instance, the amplitude and shape of blood pressure wave formations within various portions of the human cardiovascular must be assessed, such as right atrium and ventricle pressures, pulmonary arterial/pulmonary wedge pressures, systemic arterial pressures, and the like. Conventional monitoring systems, such as are disclosed in U.S. Pat. Nos. 3,675,891 and 4,192,303, include an indwelling catheter connected to a transducer, which in turn is connected to a pressure monitor. The fluid-filled catheter and connecting tubing transmit the mechanical energy of the cardiovascular waveform to a diaphragm of the pressure transducer. The movement of the diaphragm in turn effects variation in an electrical function which is transformed by an amplifier to a visual display on an oscilloscope or strip chart recorder. In order to allow reliable functioning of the system over long periods of time, it is necessary to provide a continuous regulated small-volume flow of a blood anticoagulant (such as heparin) or like medical fluid to prevent occlusion of the intravascular end of the catheter by blood coagulation. A large-volume flushing flow of fluid is necessary to establish fluid within the system when setting up, or to flush clots or air bubbles should they occur during monitoring.

While prior art assemblies have functioned generally satisfactorily, there have been a number of drawbacks associated therewith. For instance, some flow regulating assemblies have had excessive turbulence and air bubble entrapment associated therewith, necessitate the use of both an operator's hands when fast flushing, differential seatings of the valve being provided before and after fast-flush (resulting in a variance of the small-volume flow rates), quality control problems during fabrication, inability to provide adjustment of the small-volume flow rate from the exterior of the assembly, inability to re-use the assembly, and relatively expensive resistor designs. Further, as indicated by Schwartz et al in the March-April 1977 issue of *Critical Care Medicine* in an article entitled "A Hazard of the Intraflow Continuous System", occasional false high pressure recording due to the pressure head in the flush container affecting transducer readings can occur.

According to the present invention, a flow regulating assembly and components therefor, and a method of facilitating control of a flow in a catheter system for monitoring hemodynamic functions, are provided that eliminate all of the above-mentioned drawbacks. According to the present invention, it is possible to fit components of the flow regulating assembly together without gluing or welding so that the assembly may be cleaned after use and re-used, it is possible to adjust the flow rate of the regulated small-volume flow, turbulence and air entrapment are minimized by providing a straight-through large-volume flush and movement of the flow occluder completely out of the fluid flow path, and operation can be effected with only one hand. The assembly components are simple and easy to manufacture, and the entire system is relatively inexpensive yet provides improved operation.

According to one aspect of the present invention, a flow regulating assembly for providing a continuous regulated small-volume flow of a medical fluid to a a catheter system for monitoring hemodynamic functions and for providing an intermittent operator-controlled large-volume flushing flow of the fluid to the catheter system is provided. The assembly comprises a housing, a fluid inlet passage to the housing, and a fluid outlet passage from the housing directly intersecting with the fluid inlet. A fluid flow-occluding member is mounted in the housing for movement from the first position generally at the intersection of the inlet and outlet wherein flow between the inlet and outlet is occluded, to a second position completely out of the path of fluid flow so that a flushing flow of fluid from the inlet to the outlet takes place. A restricting passageway is defined in the flow-occluding member so that when the member is in the first position a small-volume continuous regulated flow of fluid from the inlet through the occluding member to the outlet takes place. The flow-occluding member is mounted for reciprocal movement from the first position to the second position, with the path of reciprocal movement preferably making an angle of about 30°–60° with the inlet.

According to another aspect of the assembly according to the present invention, the flow-occluding member actuating means is mounted exteriorly of the housing, and the restricting passageway in the flow-occluding member is defined by a small inlet passage to the flow-occluding member, a small outlet passage from the flow-occluding member (the inlet and outlet passageways intersecting in the flow-occluding member) and a needle-valve means distinct from the flow-occluding member disposed at the intersection between the small inlet and outlet passageways for providing a restriction between the small inlet and outlet passageways. The valve means preferably is provided by a screw having a conical tip and positioned concentric with the flow-occluding member and reciprocal in the same path as the flow-occluding member, and with respect to the flow-occluding member. Adjustment of the needle-valve screw is provided from the exterior of the housing by simple utilization of a screwdriver.

According to another aspect of the present invention, a valve element for use in the flow regulating assembly is provided. The valve element includes an elongated piston having a first end portion and a second end portion with a first sealing member exterior of the piston member first end portion and a second sealing member exterior of the second piston member second end portion. A central passageway is defined in the piston member from the first end to the second end thereof generally parallel to the dimension of elongation of the piston member. A fluid inlet passageway is defined in the piston member between the first and second sealing members and intersecting the central passageway, so that fluid entering the inlet passageway between the sealing members in the dimension of elongation of the piston may flow into the central passageway. The element further comprises a needle-valve means and means for mounting the needle-valve means in the central passageway on the opposite side of the fluid inlet as the second sealing member and at the intersection between the inlet passageway and the central passageway for providing a fluid restriction between the inlet passageway and central passageway. A screw with a conical tip provides the needle-valve means and preferably the central passageway has a large diameter than the piston member first portion than in the second portion.

A method of facilitating control of a flow for providing a continuous regulated small-volume flow or an intermittent operator-controlled large-volume flushing flow of a medical fluid to a catheter system for monitoring hemodynamic functions is also provided according to the present invention. The method includes the steps of (a) sterilizing the assembly components and (b) fitting the assembly components together in a clean room to provide a sterile complete assembly, without welding or gluing of the components. The method further comprises the steps of sequentially (c) operatively connecting the assembly to a catheter system, flush container, and transducer; (d) operating the assembly to provide a large-volume flushing flow of fluid; (e) unconnecting the assembly from the catheter system, flush container, and transducer; and (f) repeating steps (a), (b) and (c) using the same assembly components. The method also comprises the further step of, after step (c), (g) effecting adjustment of the volume of the continuous regulated small-volume flow from exteriorly of the assembly housing and without affecting the sterility of the assembly.

It is the primary object of the present invention to provide a simple and effective assembly, components, and method adapted to provide a continuous regulated small-volume or an intermittent operator-controlled large-volume flushing flow of a medical fluid to a catheter system for monitoring hemodynamic functions. This and other objects of the invention will become clear from an inspection of the detailed description of the invention, and from the appended claims.

BRIEF DESCRIPTION OF THE DRAWINGS

FIG. 3 is a view like FIG. 2 only illustrating a slightly modified assembly, and in the large-volume flushing flow mode thereof;

FIG. 4 is a side view, partly in cross-section and partly in elevation, of an exemplary flow-occluding piston member utilizable in the apparatus of FIG. 2;

FIG. 5 is a perspective view of components of the piston member actuator of the exemplary assembly; and FIG. 6 is a side view of a modified form of the assembly according to the present invention.

DETAILED DESCRIPTION OF THE DRAWINGS

Figure 1:
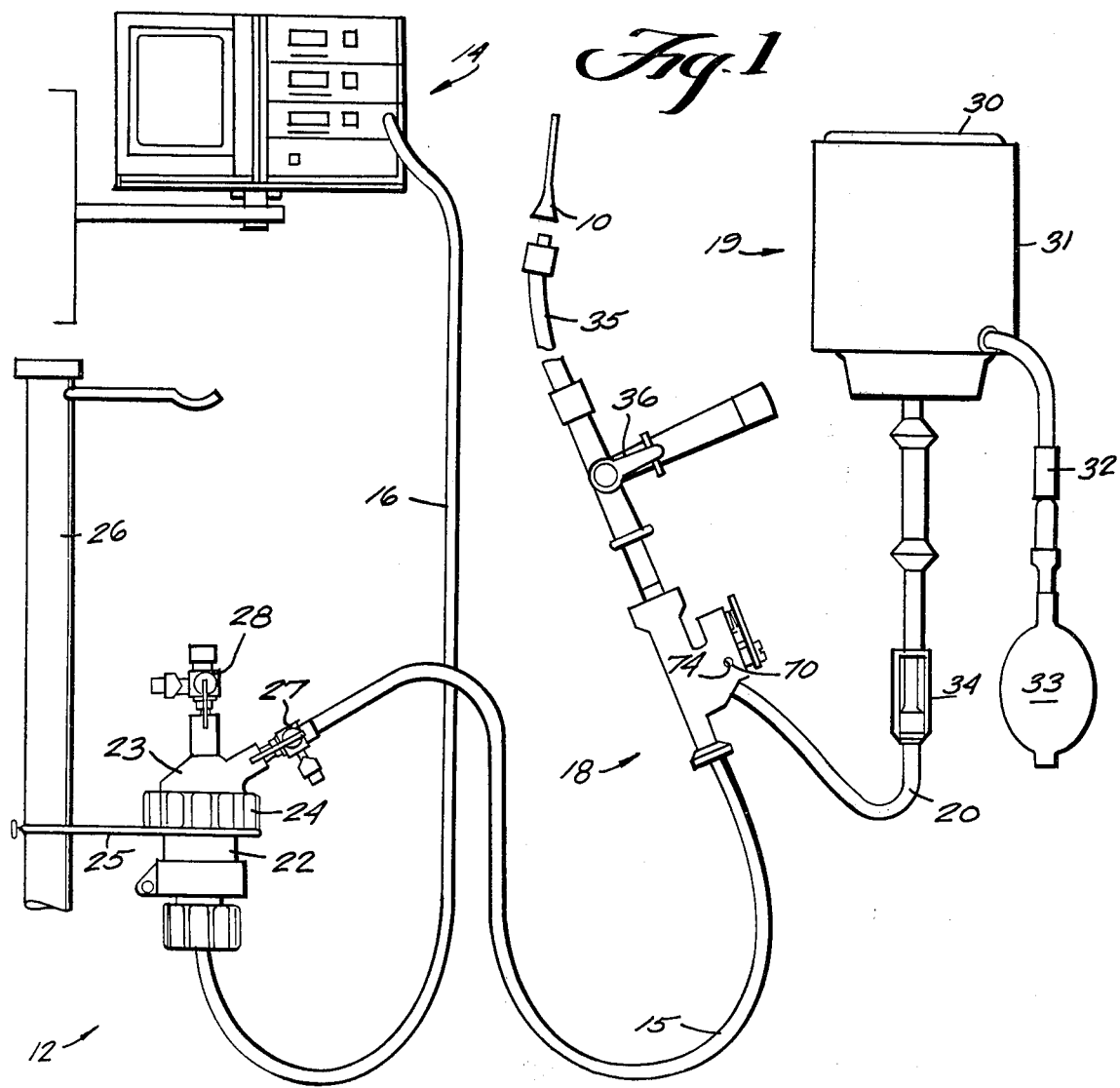
FIG. 1 is a side view illustrating an exemplary assembly according to the present invention connected up in its operating environment.

A catheter system for monitoring hemodynamic functions, such as arterial pulse waveform, stroke volume, heart rate, cardiac output, diastolic and mean pressures, etc., is illustrated in FIG. 1. The system is conventional except for the use of the particular flow regulating assembly (18) according to the present invention. The main components of the system include an intravenous or intraarterial, intracardiac catheter 10, pressure transducer 12, pressure monitor 14, pressure tubing 15, and transducer cable 16. The flow regulating assembly 18 is mounted in operative association with the pressure tubing 10 leaning from transducer 12, and is connected up to a source of medical fluid (such as a heparin solution) 19 by I.V. tubing 20.

The transducer 12 includes a body 22, a dome 23, and a dome fixation ring, nut, and washer assembly 24. The transducer 12 is mounted by transducer holder 25 to an I.V. pole 26 or the like. The transducer dome 23 conventionally has two 3-way stopcocks 27, 28 associated therewith. Stopcock 27 is utilized during normal hemodynamic function monitoring, while stopcock 28 is connectable up to a manometer system to provide physical testing of the system.

The medical fluid supply 19 includes a fluid container 30 mounted in a blood pressure bag unit 31, with a pressure bulb 33 interconnected by tubing 32 to the container-unit system 30, 31. A flow restrictor or clamp 34 may be provided in tubing 20 between the structure 19 and the flow regulating assembly 18. Pressure tubing 35 interconnects the flow regulating assembly 18 to the catheter 10, with a 3-way stopcock 36 disposed therein.

Figure 2:
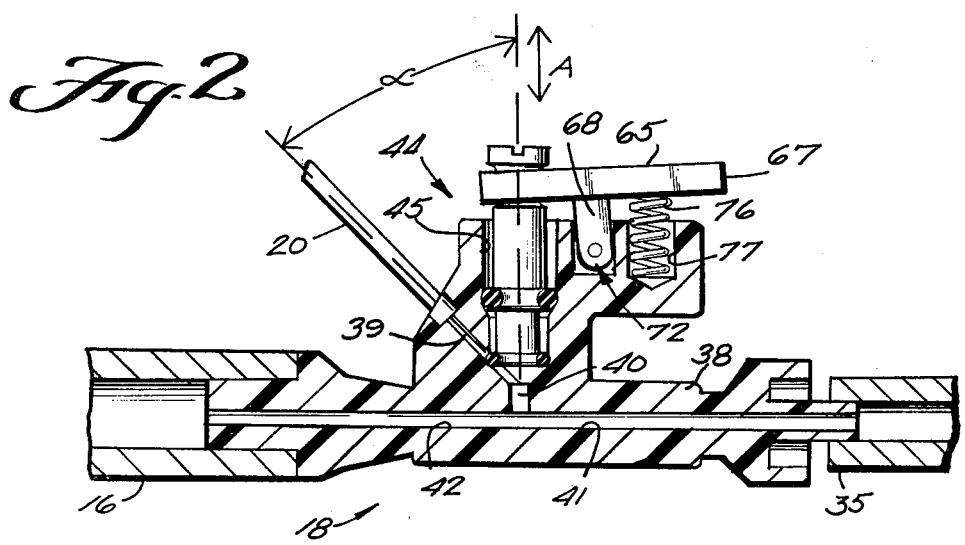
FIG. 2 is a side view, partly in cross-section and partly in elevation, of an exemplary assembly according to the present invention in the continuously small-volume flow mode thereof.

The advantageous flow regulating assembly 18 according to the present invention is illustrated most clearly in FIGS. 2 through 5. The assembly 18 includes a housing 38 with means defining a fluid inlet passage 39 into the housing, and means defining a fluid outlet passage 40 from the housing, the passage 40 directly intersecting the inlet 39. The outlet passage 40 may be constructed, as illustrated in FIG. 2, so that it has a single stem portion which branches to two branches 41, 42, the outlet branch 41 leading to the tubing 35 and ultimately the patient, and the outlet branch 41 leading to the tubing 16 and ultimately the transducer 12. Alternatively, as shown in FIG. 3, the inlet 39 can terminate directly in branches 41,42, making the flow path simpler, and reducing turbulence.

The assembly 18 further includes a fluid flow-occluding member, such as piston member, shown generally at 44. An elongated bore 45 formed in housing 38 and cooperating exterior surface portions of the piston member 44 provide means for mounting the member 44 in the housing 38 for movement from a first position (FIG. 2) to a second position (FIG. 3). In the first position, the member 44 occludes fluid flow between the inlet 39 and outlet branches 41, 42. In the second position, the flow-occluding member 44 is completely out of the path of the fluid flow from the inlet 39 to outlet branches 41, 42 so that a large-volume flushing flow of fluid from the inlet to the outlet takes place. In this way, no cavities are provided in the fast-flush path, and the flow does not travel around a valving component in the fast-flush mode. Thus, turbulence and entrapment of air bubbles are minimized.

The member 44, as illustrated most clearly in FIGS. 2 through 4, is elongated and has a first end portion 47 having a first cross-sectional area, and a second end portion 48 having a second cross-sectional area. Preferably the bore 45 in housing 38 is formed, and the member 45 is constructed, so that the first end 47 cross-sectional area is larger than the second end 48 cross-sectional area. The member 44 further comprises a first sealing member, such as O-ring 49, exterior of the first end portion 47 (preferably adjacent the interface between the end portions 47, 48 when they have differing cross-sectional areas), and a second sealing member such as O-ring 50 exterior of the second end portion 48. The members 49, 50 provide sealing between the member 44 and bore 45 when relative movement therebetween takes place. The member 49 always prevents flow of fluid from inlet 39 out of the housing 38 through bore 45, while the O-ring 50 prevents fluid flow directly between inlet 39 and outlet 40 when seated (FIG. 2), while faciltating prevention of fluid flow out of bore 45 when unseated (FIG. 3). The member 44 is preferably mounted by bore 45 for reciprocal movement in dimension A, along the axis of elongation thereof. Rotation between the member 44 and the housing 38 is prevented by keying means such as an oval configuration of the exterior of member 44, or the elongated key 51 illustrated in FIG. 4. Key 51 cooperates with an appropriate key slot (not shown) in communication with bore 45 in housing 38.

In order to provide a continuous regulated small-volume flow of medical fluid, the system 18 further comprises means defining a restricting passageway in the flow-occluding member 44. As illustrated in FIG. 4, the restricting passageway preferably comprises means defining a fluid inlet 53 in the member 54 between the O-rings 49, 50 along the axis of elongation of the member 44, and means defining a central passageway 54 in the member 44 from the first end 47 to the second end 48 thereof, generally parallel to the dimension of elongation A of the piston member 44, and preferably concentric therewith. The central passageway 54 includes outlet portion 55 which opens on the opposite side of O-ring 50 as the O-ring 49.

In order to provide restriction of the fluid flowing in the passageway 53, 53, a needle-valve means is provided. The needle-valve means preferably comprises the conical tip 56, and means are provided for mounting the conical tip 56 in the central passage 54 on the opposite side of the fluid inlet 53 as the second sealing member 50 and at the intersection between the inlet passageway 53 and the central passageway 54 (outlet 55 thereof). Preferably the amount of restriction provided by the conical tip 56 is adjustable from exteriorly of the housing 38, and this is accomplished by making the needle-valve a screw 57 having a screw slot 58 formed in the head thereof opposite the conical tip 56, and providing as the mounting means for the needle-valve cooperating external threads 59 on the screw 57, and internal threads 60 in central bore 54. An O-ring 61 or like sealing member prevents flow of fluid through inlet 53 and through central passageway 54 past the body of screw 57 and out the housing 38.

The provision of the occluding member 44 with its various passageways 53, 54 and flowing restricting adjusting tip 56 has many advantages compared to conventional structures. Since resistance is accomplished within such a small area, the inlet 39 can be close to the tip occluder, allowing the same inlet channel 39 for the fast-flow mode and the slow-flow mode. The inlet passageway 39 and dimension of reciprocation A of the member 44 are preferably disposed at an angle α (see FIG. 2) of about 30°–60° (e.g., 45°) facilitating the fast-flush mode advantages described above by preventing any dead space within the housing 38. There are no marine-bore capillary tubes in the flow path, which tubes are difficult to manufacture and maintain and prevent re-use of the assembly. The adjustability of the slow-flow rate from exteriorly of the housing 38 is a great advantage ensuring constant desired flow rate, facilitating re-use of the assembly, and ensuring superior quality control.

In order to effect actuation of the member 44 to move it between the slow-flow (FIG. 2) and fast-flow (FIG. 3) modes, an actuating means is provided. The actuating means preferably is mounted exteriorly of the housing 38. Preferably the actuating means includes a lever 65 (see FIGS. 2 and 5 in particular) having first and second ends 66, 67 thereof and a lever extension 68 intermediate the ends 66, 67. The end 66 is slotted, as indicated at 69 in FIG. 5, and is mounted between the screw head of screw 57 and the body of member 44, as illustrated in FIGS. 2 and 3. The lever 65 is pivotally mounted by pivot pin 70. Lever extension 68 is received within a cavity 72 (see FIG. 2) in housing 38, the extension 68 having a bore 73 formed therein perpendicular to the dimension of elongation of lever 65 and (when in use) the dimension A. The housing 38 also has a bore 74 formed therein coextensive with the bore 73, the housing bore 74 preferably extending completely through the housing 38. When lever extension 68 is mounted in cavity 72, the bores 73, 74 align and the pin 70 may be inserted therethrough.

A guard 74 may be provided for lever 65 (see dotted line structure in FIG. 5). The guard 75 prevents accidental operation of lever 65 to effect fast flush if the pin 70 breaks or the patient rolls over on lever 65.

Spring biasing means are provided for normally biasing the lever 65 to move the member 44 to its slow-flow, first, position (FIG. 2). The spring biasing means may comprise a coil spring 76, mounted in a cavity 77 (see FIG. 2) of housing 38 on the opposite side of cavity 72 as the bore 45, and formed so that the spring 76 is exterior of the housing 38. By providing the spring 76 exterior of the housing 38, the dead space or the like that normally necessarily results from the use of a biasing means within the housing (and communicating with the flow passageways) is avoided, and also access to the spring biasing means to allow replace or modification thereof is readily provided. However, the spring bias may be provided by a spring, elastic member, or the like mounted in a specifically designed bore 45 if desired.

The construction of the assembly heretofore described greatly facilitates initial manufacture and assembly of the structure, and in such a manner that it can be re-used. No gluing, welding, or other bonding is required (although they may be practiced if desired) in order to construct the assembly 18, rather the components need only be fitted together. Thus, the structure 18 facilitates the following method of facilitating control of medical fluid flow in a catheter system for monitoring hemodynamic functions:

(a) The assembly components, such as housing 38, flow regulating element 44, and acutator 65, are sterilized.

(b) The assembly components are fit together in a clean room to provide a sterile complete assembly, with no welding, gluing, or like bonding of the components being necessary. The member 44, which already has the screw 57 inserted in central bore 54 thereof, is merely inserted into bore 45, spring 76 is inserted in place, lever components 69 and 68 are properly inserted in operative association with member 44 and cavity 72, and pin 70 is passed through bores 73 and 74 to complete assembly. The structure 18 may then be sterilely packaged for ultimate use.

The method according to the invention may also comprise the further steps of: (c) Operatively connecting the assembly to a catheter system, by connecting tubes 16 and 35 to the outlet passageways 42, 41, respectively, and connecting tube 20 to inlet passageway 39. (d) Operating the assembly to provide a large-volume flushing flow of fluid by pushing on lever end 67 to unseat O-ring 50 (see FIG. 3). (d) Unconnecting the assembly 18 from the catheter system (by detaching tubing 16, 20, and 35) and disassembling assembly 18. And (f) repeating steps (a), (b), and (c) using the same assembly components. This ability to re-use the assembly in a cost-effective manner is novel and very advantageous. The method also contemplates the further step of (g) effecting adjustment of the volume of the continuous regulated small-volume flow from exteriorly of the assembly housing without affecting the sterility of the assembly, such as by inserting a screwdriver blade in slot 58 and rotating screw 57 to adjust the position of conical tip 56 with respect to passageway 53 in outlet 55 from passageway 54.

In operation of the apparatus 18, in the normal mode thereof, a heparin solution from container 30 will flow into inlet 39, through passageway 53 and outlet 55 to the outlet passageway 40. When a flush of the system is necessary in order to fill and irrigate the catheter system, flush out the beginnings of clot formations, or to flush occasion air bubbles out of the system, the lever end 67 is depressed, resulting in movement of the second end 48 of piston member 44 out of the flow path from inlet 39 to outlet 40.

Another embodiment according to the present invention is illustrated in FIG. 6. Structures corresponding to those illustrated in the FIGS. 1 through 5 embodiment have the same reference numerals only with a "1" preceding the reference numeral. The housing 138 in FIG. 6 is of transparent plastic, which is a preferred material for the housing. The structure in the FIG. 6 embodiment facilitates simple attachment of flow regulator 118 to transducer 112 allowing the assembly to be utilized as an offline irrigation valve.

It will be thus be seen that according to the present invention an extremely useful flow regulating assembly for use with a catheter system for monitoring hemodynamic functions, and associated method, have been provided which eliminate the drawbacks inherent in prior art arrangements.

While the invention has been herein shown and described in what is presently conceived to be the most practical and preferred embodiment thereof, it will be apparent to those of ordinary skill in the art that modifications may be made thereof within the scope of the invention, which scope is to be accorded the broadest interpretation of the appended claims so as to encompass all equivalent assemblies and methods.

What is claimed is:

1. A flow regulating assembly for providing a continuous regulated small-volume flow of medical fluid to a catheter system for monitoring hemodynamic functions and for providing an intermittent operator-controlled large-volume flushing flow of the fluid to the catheter system, said assembly comprising:

a housing;
means defining a fluid inlet passage to said housing;
means defining a fluid outlet passage from said housing directly intersecting with said fluid inlet passage;
a fluid flow-occluding member;
means for mounting said fluid flow-occluding member in said housing for movement from a first position wherein said flow-occluding member is generally at the intersection of said inlet and outlet passages and wherein fluid flow between said fluid inlet and fluid outlet passages is occluded, to a second position wherein said flow-occluding member is moved out of the path of fluid flow from said inlet passage to said outlet passage so that intersecting imaginary straight lines extending in said inlet passage and said outlet passage do not intersect any portion of said flow-occluding member so that said flow-occluding member introduces substantially no turbulence in a flushing flow of fluid from said inlet passage to said outlet passage which tkakes place with said flow-occluding member in said second position; and
means defining a restricting passage in said flow-occluding member so that when said member is in said first position in a small-volume continuous regulated flow of fluid from said inlet passage through said occluding member to said outlet passage takes place even when said flow-occluding member is in said first position.

2. An assembly as recited in claim 1 wherein said means for mounting said fluid flow-occluding member comprises means for mounting said member for reciprocal movement from said first to said second position, and wherein said inlet and a line along said path of reciprocal movement of said flow-occluding member make an angle α of about 30°–60°.

3. An assembly as recited in claim 1 further comprising actuator means for effecting operator-controlled movement of said flow-occluding member from said first to said second positions thereof, and means for mounting said actuator means exteriorly of said housing.

4. An assembly as recited in claim 3 wherein said actuatinng means comprises a lever having first and second ends; spring biasing means mounted exteriorly of said housing; and means for pivotally mounting said lever intermediate said first and second ends thereof and exteriorly of said housing so that said first end is in operative engagement with said flow-occluding member and so that said second end is in operative engagement with said spring biasing means.

5. An assembly as recited in claim 3 wherein said means defining a restricting passageway in said flow-occluding member comprises means defining a small inlet passageway to said member and a small outlet passageway from said member, said inlet and outlet passageways intersecting within said member, and a needle-valve means and means for mounting said needle-valve means disposed at the intersection between said small inlet and outlet passageways for providing a restriction between said small inlet and outlet passageways.

6. An assembly as recited in claim 5 further comprising needle-valve means actuating means for effecting adjustment of the position of said needle-valve means with respect to said inlet and outlet passageways so that the flow between said small inlet and outlet passageways is adjusted, and means for mounting said needle-valve means actuating means for actuation exteriorly of said housing.

7. An assembly as recited in claim 6 wherein said means for mounting said flow-occluding member comprises means for keying said member to said housing and for mounting said member for reciprocal movement from said first to said second positions along a predetermined path, and wherein means for mounting said needle-valve means mounts said needle-valve means for reciprocal movement along the same path as the reciprocal path of movement of said flow-occluding member.

8. An assembly as recited in claim 1 wherein said means defining a restricting passageway in said flow-occluding member comprises means defining a small inlet passageway to said member and a small outlet passageway from said member, said inlet and outlet passageways intersecting within said member, and a needle-valve means and means for mounting said needle-valve means disposed at the intersection between said small inlet and outlet passageways for providing a restriction between said small inlet and outlet passageways.

9. An assembly as recited in claim 8 further comprising needle-valve means actuating means for effecting adjustment of the position of said needle-valve means with respect to said inlet and outlet passageways so that the flow between said small inlet and outlet passageways is adjusted.

10. An assembly as recited in claim 9 wherein said means for mounting said flow-occluding member comprises means for keying said member to said housing and for mounting said member for reciprocal movement from said first to said second positions along a predetermined path, and wherein means for mounting said needle-valve means mounts said needle-valve means for reciprocal movement along the same path as the reciprocal path of movement of said flow-occluding member, and further comprising means for mounting said needle-valve means actuating means for actuation exteriorly of said housing.

11. A flow regulating assembly for providing a continuous regulated small-volume flow of a medical fluid to a catheter system for monitoring hemodynamic functions and for providing an intermittent operator-controlled large-volume flushing flow of the fluid to the catheter system, said assembly comprising:
a housing;
means defining a fluid inlet passage to said housing;
means defining a fluid outlet passage from said housing;
a fluid flow-occluding member;
means for mounting said flow-occluding member in said housing for movement from a first position wherein said flow-occluding member occludes flow between said inlet and outlet, and a second position wherein said occluding member allows flow between said inlet and said outlet;
actuating means for effecting operator-controlled movement of said flow-occluding member from said first to said second positions thereof;
means for mounting said flow-occluding member actuating means exteriorly of said housing; and
means for defining a restricting passageway in said flow-occluding member so that when said member is in said first position a small-volume continuous regulated flow of fluid from said inlet passage through said flow-occluding member to said outlet passage takes place; said means comprising a small inlet passageway to said flow-occluding member and a small outlet passageway from said flow-occluding member, said inlet and outlet passageways intersecting in said flow-occluding member and said passageways distinct from said inlet and outlet passages; and a flow restrictor distinct from said flow-occluding member disposed at the intersection between said small inlet and outlet passageways for providing a restriction between said small inlet and outlet passageways.

12. An assembly as recited in claim 11 wherein said flow restrictor comprises a needle-valve means, and further comprising needle-valve means actuating means for effecting adjustment of the position of said needle-valve means with respect to said inlet and outlet passageways so that the flow between said small inlet and outlet passageways is adjusted, and means for mounting said needle-valve means actuating means for actuation exteriorly of said housing.

13. An assembly as recited in claim 12 wherein said means for mounting said flow-occluding member comprises means for keying said member to said housing and for mounting said member for reciprocal movement from said first to said second positions along a predetermined path, and wherein means for mounting said needle-valve means mounts said needle-valve means for reciprocal movement along the same path as the reciprocal path of movement of said flow-occluding member.

14. An assembly as recited in claims 12 or 13 wherein said actuating means comprises a lever having first and second ends; spring biasing means mounted exteriorly of said housing; and means for pivotally mounting said lever intermediate said first and second ends thereof and exteriorly of said housing so that said first end is in operative engagement with said flow-occluding member and so that said second end is in operative engagement with said spring biasing means.

15. A flow regulating assembly for providing a continuous regulated small-volume flow of medical fluid to a catheter system for monitoring hemodynamic functions and for providing an intermittent operator-controlled large-volume flushing flow of the fluid to the catheter system, said assembly comprising:
a housing;
means defining a fluid inlet passage to said housing;
means defining a fluid outlet passage from said housing directly intersecting with said fluid inlet;
a fluid flow-occluding member;
means for mounting said fluid flow-occluding member in said housing for movement from a first position wherein said flow-occluding member is generally at the intersection of said inlet and outlet and wherein fluid flow between said fluid inlet and fluid outlet is occluded, to a second position wherein said flow-occluding member is moved generally out of the path of fluid flow from said inlet to said outlet so that a flushing flow of fluid from said inlet to said outlet takes place;
means defining a restricting passage in said flow-occluding member so that when said member is in said first position a small-volume continuous regulated flow of fluid from said inlet through said occluding member to said outlet takes place; and
actuator means for effecting operator-controlled movement of said flow-occluding member from said first to said second positions thereof, and means for mounting said actuator means exteriorly of said housing, said actuator means comprising: a lever having first and second ends; spring biasing means mounted exteriorly of said housing; and means for pivotally mounting said lever intermediate said first and second ends thereof and exteriorly of said housing so that said first end is in operative engagement with said flow-occluding member and so that said second end is in operative engagement with said spring biasing means.

16. An assembly as recited in claim 15 wherein said means for pivotally mounting said lever comprises means defining a through-extending bore in said housing; a lever extension integral with said lever intermediate the ends thereof; means for defining an elongated lever-extension-receiving cavity in said housing so that the dimension of elongation of said cavity is substantially perpendicular to said bore; and a pivot pin having an outside diameter slightly less than the diameter of said bore, said pin passing through said lever extension and said housing disposed in said bore.

17. A flow regulating assembly for providing a continuous regulated small-volume flow of a medical fluid to a catheter system for monitoring hemodynamic functions and for providing an intermittent operator-controlled large-volume flushing flow of the fluid to the catheter system, said assembly comprising:

a housing;
means defining a fluid inlet passage to said housing;
means defining a fluid outlet passage from said housing;
a fluid flow-occluding member;
means for mounting said flow-occluding member in said housing for movement from a first position wherein said flow-occluding member occludes flow between said inlet and outlet, and a second position wherein said occluding member allows flow between said inlet and said outlet;
actuator means for effecting operator-controlled movement of said flow-occluding member from said first to said second positions thereof;
means for mounting said flow-occluding member actuating means exteriorly of said housing; and
means for defining a restricting passageway in said flow-occluding member so that when said member is in said first position a small-volume continuous regulated flow of fluid from said inlet through said flow-occluding member to said outlet takes place; said means comprising a small inlet passageway to said flow-occluding member and a small outlet passageway from said flow-occluding member, said inlet and outlet passageways intersecting in said flow-occluding member; and a flow restrictor distinct from said flow-occluding member disposed at the intersection between said small inlet and outlet passageways for providing a restriction between said small inlet and outlet passageways;
said actuator means comprising: a lever having first and second ends; spring biasing means mounted exteriorly of said housing; and means for pivotally mounting said lever intermediate said first and second ends thereof and exteriorly of said housing so that said first end is in operative engagement with said flow-occluding member and so that said second end is in operative engagement with said spring biasing means.

18. An assembly as recited in claim 17 wherein said means for pivotally mounting said lever comprises means defining a through-extending bore in said housing; a lever extension integral with said lever intermediate the ends thereof; means for defining an elongated lever-extension-receiving cavity in said housing so that the dimension of elongation of said cavity is substantially perpendicular to said bore; and a pivot pin having an outside diameter slightly less than the diameter of said bore, said pin passing through said lever extension and said housing disposed in said bore.

* * * * *